(12) United States Patent  
Kabasawa

(10) Patent No.: US 8,498,690 B2  
(45) Date of Patent: Jul. 30, 2013

(54) BLOOD FLOW DYNAMIC ANALYSIS APPARATUS, METHOD OF BLOOD FLOW DYNAMIC ANALYSIS, AND MAGNETIC RESONANCE IMAGING SYSTEM

(75) Inventor: Hiroyuki Kabasawa, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 608 days.

(21) Appl. No.: 12/766,663

(22) Filed: Apr. 23, 2010

(65) Prior Publication Data

US 2010/0274119 A1    Oct. 28, 2010

(30) Foreign Application Priority Data

Apr. 24, 2009  (JP) .................................. 2009-106133  
Feb. 3, 2010   (JP) .................................. 2010-021698

(51) Int. Cl.  
*A61B 5/055* (2006.01)

(52) U.S. Cl.  
USPC .......................................... 600/419; 600/420

(58) Field of Classification Search  
None  
See application file for complete search history.

(56) References Cited

U.S. PATENT DOCUMENTS

| 2006/0215889 A1* | 9/2006 | Omi et al. ..................... 382/128 |
| 2006/0241402 A1 | 10/2006 | Ichihara et al. |
| 2008/0262344 A1* | 10/2008 | Brummett ..................... 600/426 |
| 2009/0129536 A1 | 5/2009 | Ichihara et al. |

FOREIGN PATENT DOCUMENTS

JP    2007-068852    3/2007

* cited by examiner

*Primary Examiner* — Jacqueline Cheng  
(74) *Attorney, Agent, or Firm* — Armstrong Teasdale LLP

(57) ABSTRACT

A blood flow dynamic analysis apparatus analyzes the kinetics of a blood flow in a subject by injecting a contrast medium into the subject. The apparatus includes a map generation device computing the value of a parameter related to time change in the concentration of the contrast medium injected into the subject and generating a map of the parameter, and a display condition determination device determining a display condition for the map based on a threshold value of the parameter for discriminating between a lesion region where a lesion exists and an unaffected region where no lesion exists in the map.

8 Claims, 13 Drawing Sheets

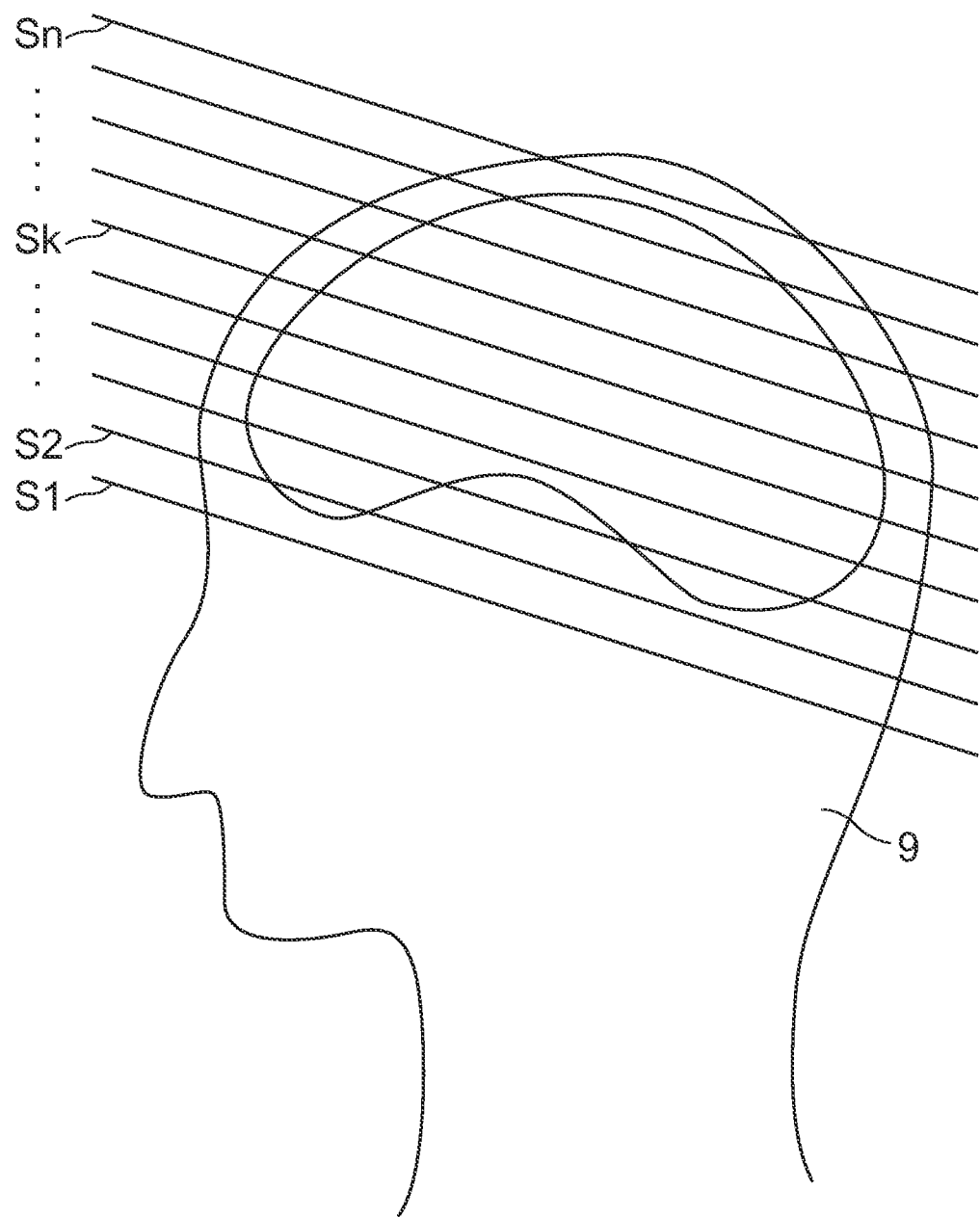

FIG. 6B
TTP
MTT
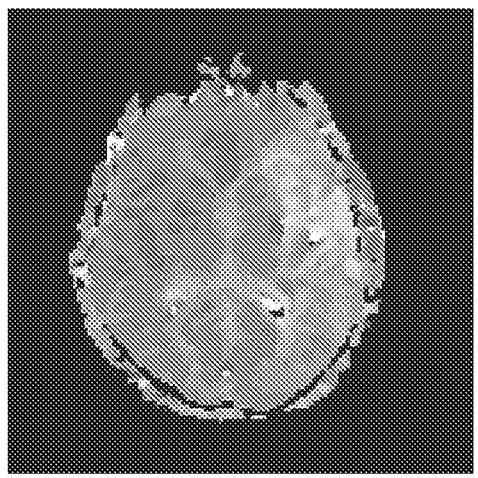
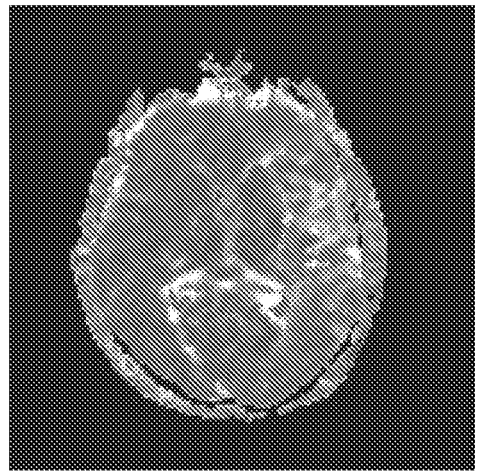

Diagrammatic sketch of TTP map

Diagrammatic sketch of TTP map

FIG. 12

|  | TTP | MTT |
|---|---|---|
| A2 | 5 sec | 4.8 sec |

FIG. 13
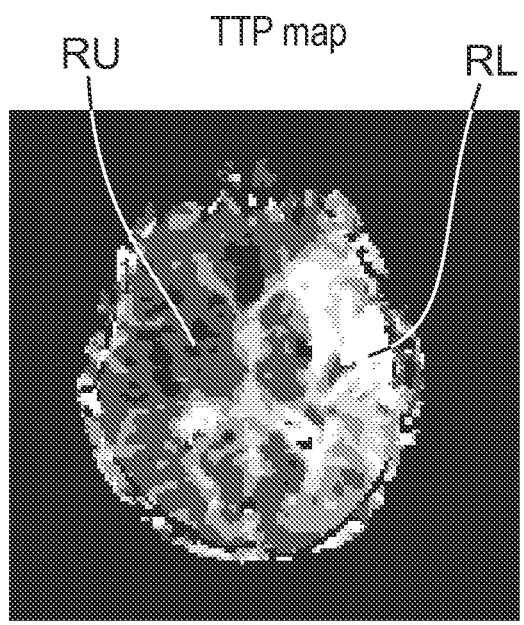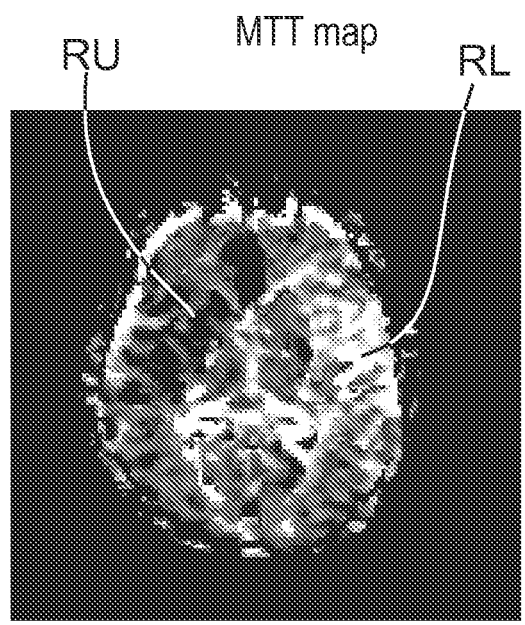

BLOOD FLOW DYNAMIC ANALYSIS APPARATUS, METHOD OF BLOOD FLOW DYNAMIC ANALYSIS, AND MAGNETIC RESONANCE IMAGING SYSTEM

CROSS REFERENCE TO RELATED APPLICATIONS

This application claims the benefit of Japanese Patent Application No. 2009-106133 filed Apr. 24, 2009, and Japanese Patent Application No. 2010-021698 filed Feb. 3, 2010, both of which are hereby incorporated by reference in their entirety.

BACKGROUND OF THE INVENTION

The present invention relates to a blood flow dynamic analysis apparatus for analyzing the kinetics of a blood flow in a subject, a method of a blood flow dynamic analysis, and a magnetic resonance imaging system.

As a method for determining a display condition for a contrast MR perfusion image, the following method is known: an operator sets ROI of unaffected hemisphere in a map (for example, a map of contrast medium arrival time) displayed on a screen and the pixel values in the ROI are used to determine a display condition.

In addition, a method of using a histogram to determine a display condition is also known. (Refer to Japanese Unexamined Patent Publication No. 2007-68852.)

However, the images displayed by the method in Patent Document 1 involve a problem. The boundary between a lesion region where some lesion is present and an unaffected region where no lesion is present is prone to become unclear and it takes time to identify the lesion region.

It is desirable that the problem described previously is solved.

BRIEF DESCRIPTION OF THE INVENTION

In one aspect, a blood flow dynamic analysis apparatus analyzes the kinetics of a blood flow in a subject by injecting a contrast medium into the subject, and includes a map generation device that computes the value of a parameter related to time change in the concentration of the contrast medium injected into the subject and generates a map of the parameter; and a display condition determination device that determines a display condition for the map based on a threshold value of the parameter for discriminating between a lesion region where some lesion is present and an unaffected region where no lesion is present in the map.

In another aspect, a blood flow dynamic analysis method is provided for analyzing the kinetics of a blood flow in a subject by injecting a contrast medium into the subject, and includes a map generation step at which the value of a parameter related to time change in the concentration of the contrast medium injected into the subject and a map of the parameter is generated; and a display condition determination step at which a display condition for the map is determined based on a threshold value of the parameter for discriminating between a lesion region where a lesion is present and an unaffected region where no lesion is present in the map.

In yet another aspect, a program is provided for analyzing the kinetics of a blood flow in a subject by injecting a contrast medium into the subject and causes a computer to carry out: map generation processing of computing the value of a parameter related to time change in the concentration of the contrast medium injected into the subject and generating a map of the parameter; and display condition determination processing of determining a display condition for the map based on a threshold value of the parameter for discriminating between a lesion region where a lesion is present and an unaffected region where no lesion is present in the map.

In some embodiments, a display condition for a map is determined based on a threshold value of a parameter for discriminating between an unaffected region and a lesion region in the map. Therefore, it is possible to determine a display condition so that an unaffected region and a lesion region can be visually and easily discriminated from each other.

Further objects and advantages of the present invention will be apparent from the following description of embodiments of the invention as illustrated in the accompanying drawings.

BRIEF DESCRIPTION OF THE DRAWINGS

FIG. 3 is an example of slices set on a subject 9.

FIGS. 6A and 6B are drawings explaining two maps generated with respect to each of slices S1 to Sn.

FIG. 12 is a schematic diagram indicating values stored in a storage unit 646.

FIG. 13 is a drawing illustrating a TTP map and an MTT map displayed in accordance with a window width WW and a window level WL computed at Step S48.

DETAILED DESCRIPTION OF THE INVENTION

Hereafter, detailed description will be given to an embodiment for carrying out the invention with reference to the drawings.

Figure 1:
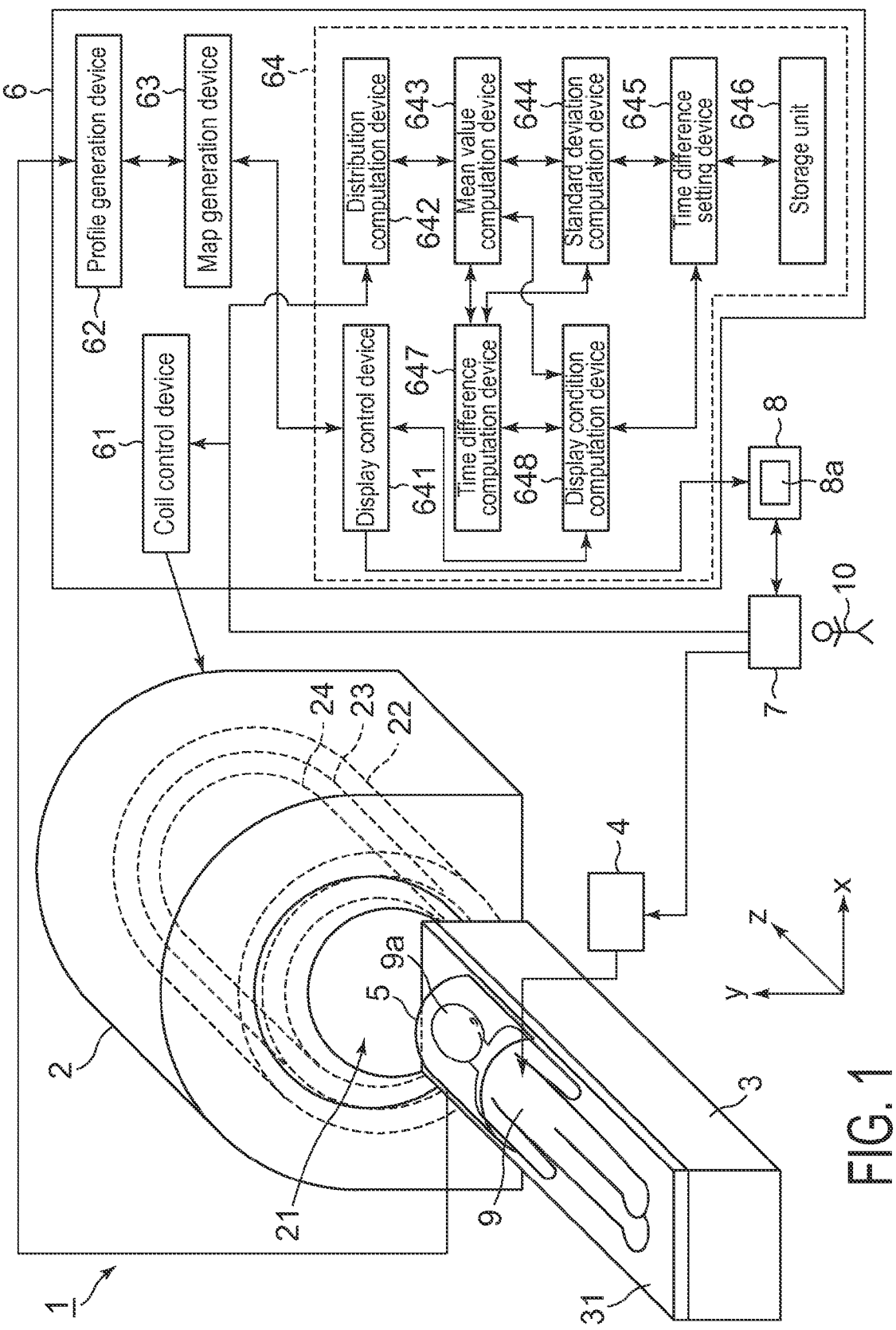
FIG. 1 is a schematic diagram of a magnetic resonance imaging system 1 in an embodiment of the invention.

FIG. 1 is a schematic diagram of a magnetic resonance imaging system 1 in an embodiment of the invention.

The magnetic resonance imaging system (hereafter, referred to as MRI (Magnetic Resonance Imaging) apparatus) 1 includes: a coil assembly 2, a table 3, a contrast medium injection device 4, a reception coil 5, a control device 6, an input device 7, and a display device 8.

The coil assembly 2 includes: a bore 21 in which a subject 9 is placed, a superconducting coil 22, a gradient coil 23, and a transmission coil 24. The superconducting coil 22 applies a static magnetic field B0; the gradient coil 23 applies a gradient pulse; and the transmission coil 24 transmits an RF pulse.

The table 3 includes a cradle 31. The cradle 31 is moved to the z direction and the −z direction. When the cradle 31 is moved to the z direction, the subject 9 is carried into the bore 21. When the cradle 31 is moved to the −z direction, the subject 9 that has been carried into the bore 21 is carried out of the bore 21.

The contrast medium injection device 4 injects a contrast medium into the subject 9.

The reception coil 5 is attached to the head 9a of the subject 9. An MR (Magnetic Resonance) signal received by the reception coil 5 is transmitted to the control device 6.

The control device 6 includes a coil control device 61, a profile generation device 62, a map generation device 63, and a display condition determination device 64.

The coil control device 61 controls the gradient coil 23 and the transmission coil 24 so that a pulse sequence for imaging the subject 9 is carried out in response to an imaging instruction inputted through the input device 7 by an operator 10.

Figure 4A:
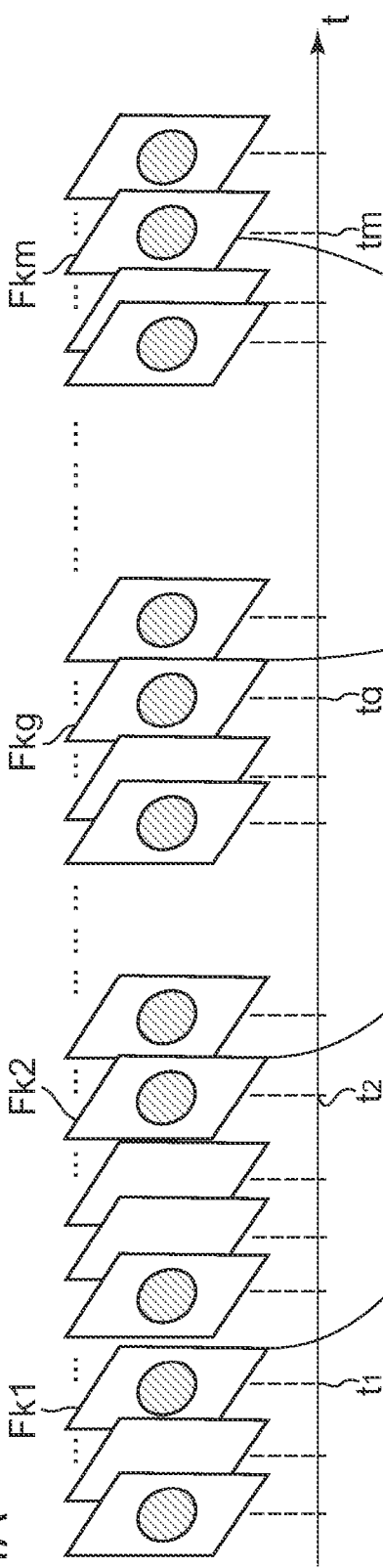
FIGS. 4A and 4B are conceptual diagrams illustrating frame images obtained from slices S1 to Sn.
Figure 4B:
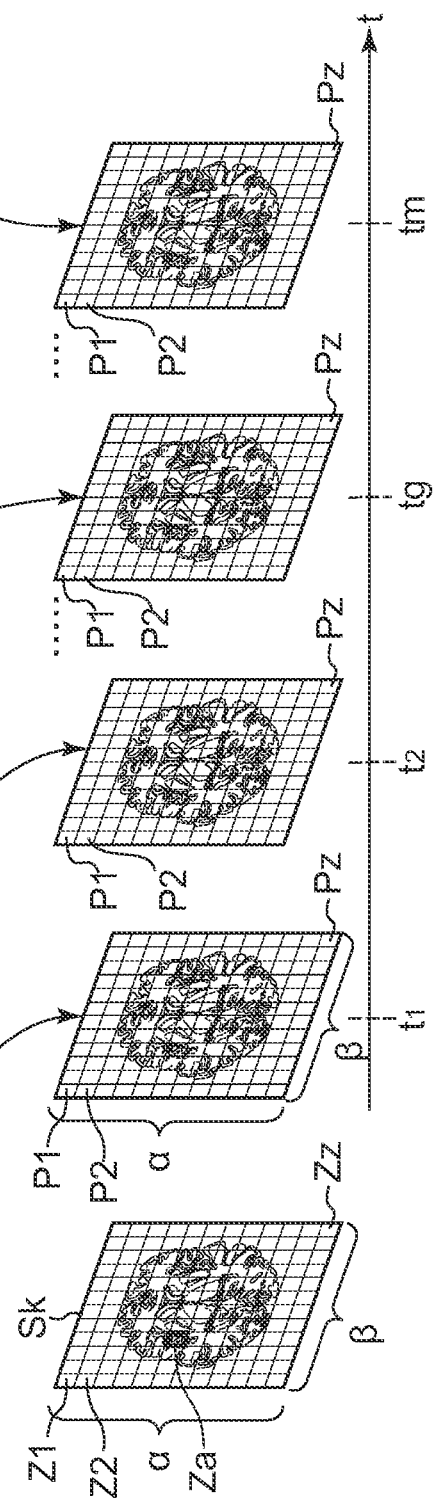

The profile generation device 62 generates a profile indicating time change in the concentration of the contrast medium with respect to each of zones Z1 to Zz (Refer to FIG. 4B) in slices S1 to Sn on the basis of data of frame images (Refer to FIG. 4B).

The map generation device 63 computes the value of a parameter related to time change in the concentration of the contrast medium from the concentration-time curve CT of the contrast medium (Refer to FIG. 5) and generates a map of the parameter.

The display condition determination device 64 includes a display control device 641, a distribution computation device 642, a mean value computation device 643, a standard deviation computation device 644, a time difference setting device 645, a storage unit 646, a time difference computation device 647, and a display condition computation device 648.

The display control device 641 controls the display device 8 so that the display device 8 displays maps (Refer to FIG. 10 and FIG. 13) and varied information.

The distribution computation device 642 computes the following distributions: a distribution of the values of peak concentration arrival time TTP of the pixels contained in a region of interest ROIt (Refer to FIG. 11) in a TTP map; and a distribution of the values of mean transit time MTT of the pixels contained in a region of interest ROIm (Refer to FIG. 11) in an MTT map.

The mean value computation device 643 computes the mean value AVE (Refer to FIG. 8A) of peak concentration arrival time TTP and the mean value of mean transit time MTT.

The standard deviation computation device 644 computes the standard deviation SD (Refer to FIG. 8A) of peak concentration arrival time TTP and the standard deviation of mean transit time MTT.

The time difference setting device 645 sets the value of time difference A2 contained in the right-hand sides of Expressions (7) and (8) described later.

The storage unit 646 stores a time difference A2 with respect to peak concentration arrival time TTP and a time difference A2 with respect to mean transit time MTT.

The time difference computation device 647 computes the value of time difference A1 contained in the right-hand sides of Expressions (7) and (8) described later.

The display condition computation device 648 computes a window width WW and a window level WL with respect to a TTP map and an MTT map.

The coil control device 61, the profile generation device 62, the map generation device 63, and the display condition determination device 64 are implemented by installing programs for carrying out the respective devices in the control device 5. However, they may be implemented only by hardware without use of a program.

The input device 7 inputs various instructions to the control device 6 according to the operation by the operator 10.

The display device 8 displays maps (Refer to FIG. 10 and FIG. 13) and varied information.

The MRI apparatus 1 is configured as mentioned above. Description will be given to the operation of the MRI apparatus 1.

Figure 2:
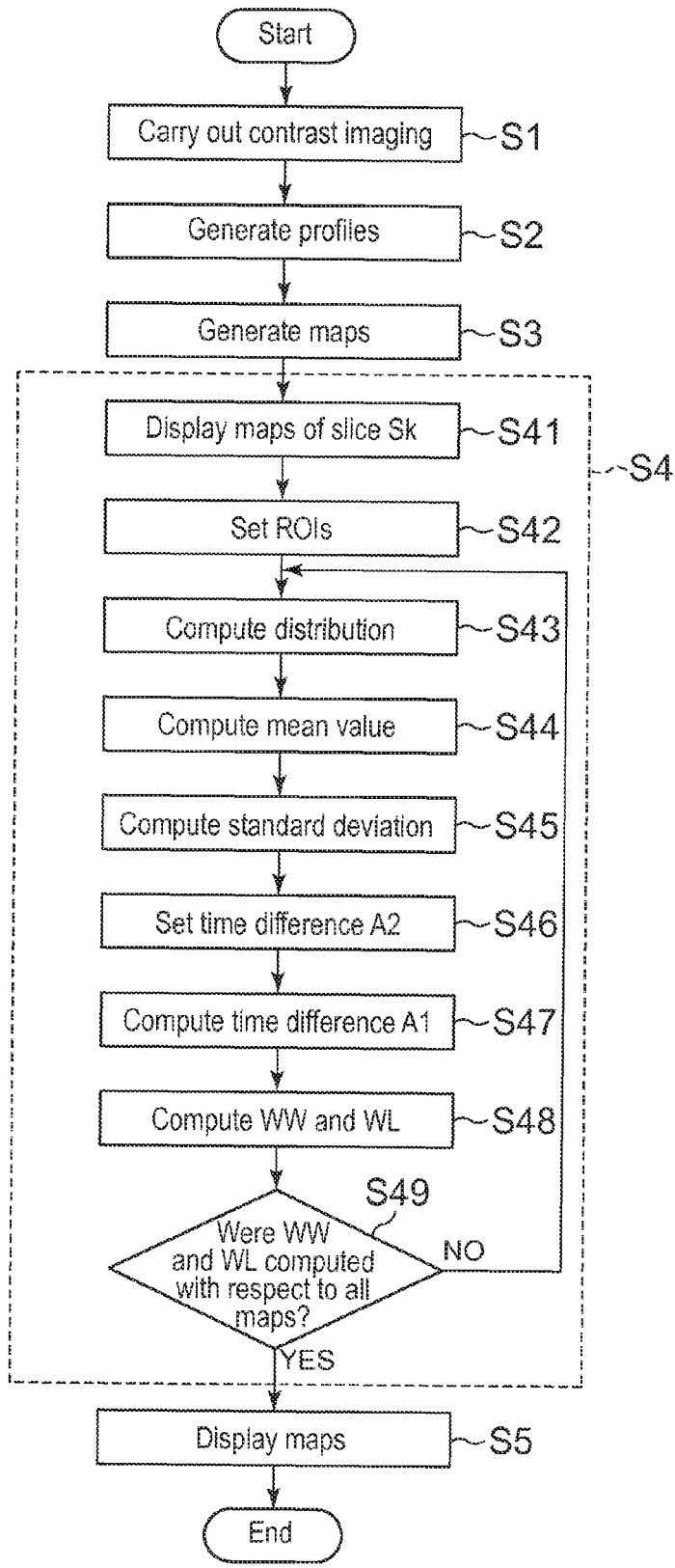
FIG. 2 is a drawing illustrating the flow of processing in an MRI apparatus 1.

FIG. 2 is a drawing illustrating the flow of processing in the MRI apparatus 1.

At Step S1, contrast imaging on the head 9a of a subject 9 is carried out. To carry out contrast imaging, an operator 10 operates the input device 7 (Refer to FIG. 1) to set slices on the subject 9.

FIG. 3 illustrates an example of slices set on the subject 9.

On the subject 9, n slices S1 to Sn are set. The number of slices is, for example, n=12. The number of slices can be arbitrarily set as required.

After setting the slices S1 to Sn, the operator 10 transmits an imaging instruction to image the subject 9 to the coil control device 61 (Refer to FIG. 1) of the MRI apparatus 1. In response to this instruction, the contrast medium injection device 4 injects a contrast medium into the subject 9. In addition, the coil control device 61 controls the gradient coil 23 and the transmission coil 24 so that a pulse sequence for imaging the head 9a of the subject 9 is carried out.

In this embodiment, a pulse sequence for obtaining m frame images from each of slices S1 to Sn is carried out by multi-slice scan. Therefore, m frame images are obtained per slice. For example, the number of frame images is m=85. Data of frame images is acquired from the slices S1 to Sn by carrying out the pulse sequence.

FIGS. 4A and 4B are conceptual diagrams illustrating frame images obtained from the slices S1 to Sn.

FIG. 4A is a schematic diagram illustrating frame images acquired from the n slices S1 to Sn set on the head 9a of the subject 9, arranged in time series in the order of acquisition. The signs FK1 to FKm are fixed to the frame images of slice Sk among the slices S1 to Sn.

The sections of the slices Sk and the m frame images FK1 to FKm acquired from the slices Sk are shown in FIG. 4B. Each frame image FK1 to FKm has a times β pixels P1, P2, . . . , Pz. The pixels P1, P2, . . . , Pz of each image frame FK1 to FKm correspond to the zones Z1, Z2, . . . , Zz.

After the execution of the processing of Step S1, the flow proceeds to Step S2.

At Step S2, the profile generation device 62 (Refer to FIG. 1) generates a profile representing time change in the concentration of the contrast medium with respect to each of the zones Z1 to Zz in each of the slices S1 to Sn on the basis of data of the frame images (Refer to FIG. 4A).

Figure 5:
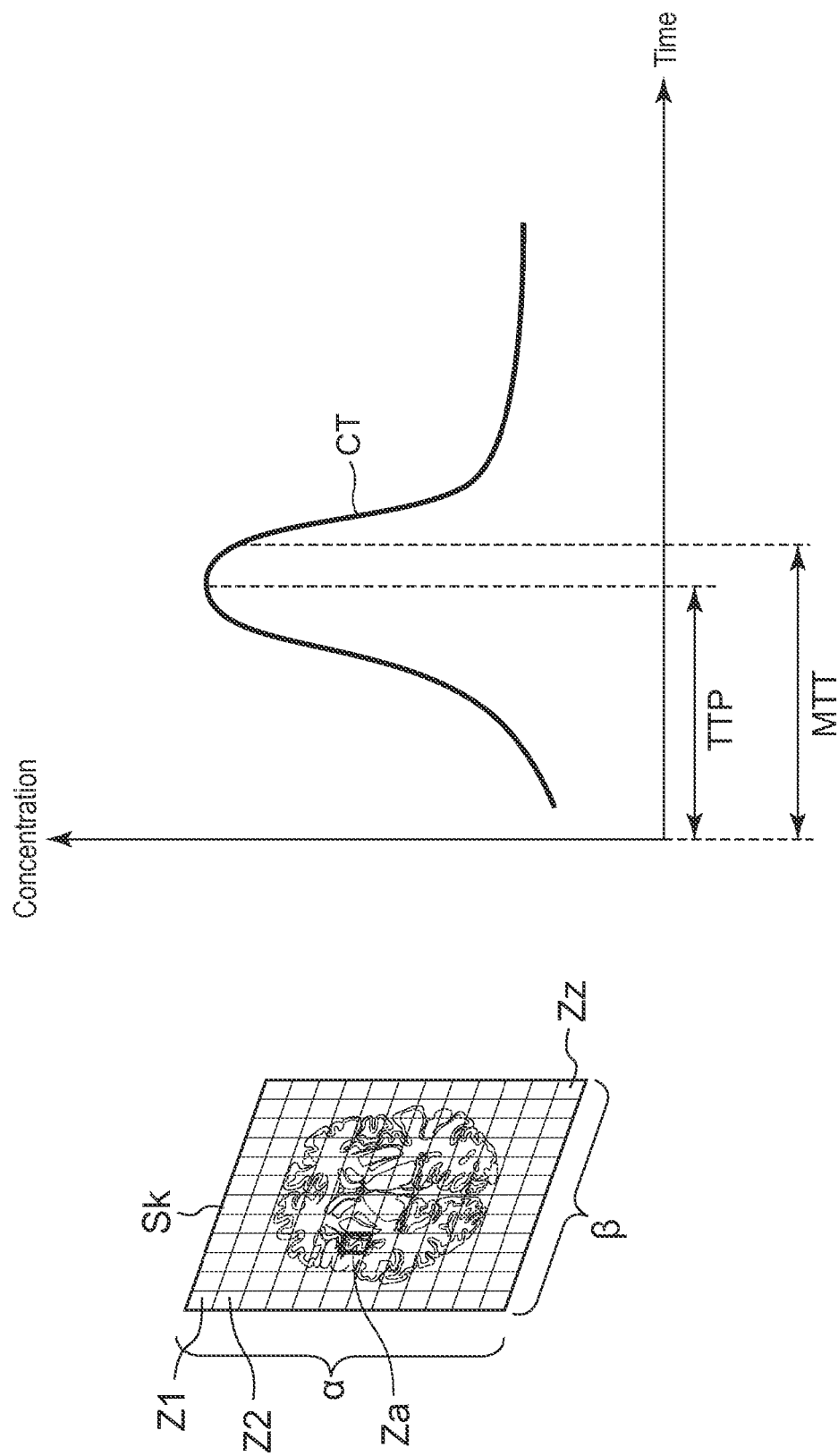
FIG. 5 is an example of a profile indicating time change in the concentration of a contrast medium.

FIG. 5 illustrates an example of a profile representing time change in the concentration of the contrast medium.

FIG. 5 shows the concentration-time curve CT of the contrast medium in the zone Za in the slice Sk. However, the concentration-time curve CT of the contrast medium is also generated with respect to the other zones in the slice Sk. Further, the concentration-time curve CT of the contrast medium is also generated with respect to each zone in the other slices.

After the generation of the concentration-time curves CT of the contrast medium, the flow proceeds to Step S3.

At Step S3, the map generation device 63 (Refer to FIG. 1) computes the value of a parameter related to time change in the concentration of the contrast medium from the concentration-time curves CT of the contrast medium and generates a map of the parameter. In this embodiment, the following two parameters are computed from the concentration-time curves CT of the contrast medium:
(1) Peak concentration arrival time TTP (Time To Peak)
(2) Mean transit time MTT (Mean Transit Time)

These parameters are well-known parameters in the field of blood flow dynamic analysis and can be computed using a publicly known method. Therefore, the concrete description of a computing procedure for the above parameters will be omitted. FIG. 5 indicates the peak concentration arrival time TTP and the mean transit time MTT in the zone Za in the slice Sk. However, the peak concentration arrival time TTP and the mean transit time MTT are also computed with respect to the other zones in the slice Sk. Further, the peak concentration arrival time TTP and the mean transit time MTT are also computed with respect to each zone in the other slices.

After the computation of peak concentration arrival time TTP and mean transit time MTT, the map generation device 63 (Refer to FIG. 1) generates two maps indicating the parameters of peak concentration arrival time TTP and mean transit time MTT. The maps are generated with respect to each of the slices S1 to Sn.

Figure 6A:
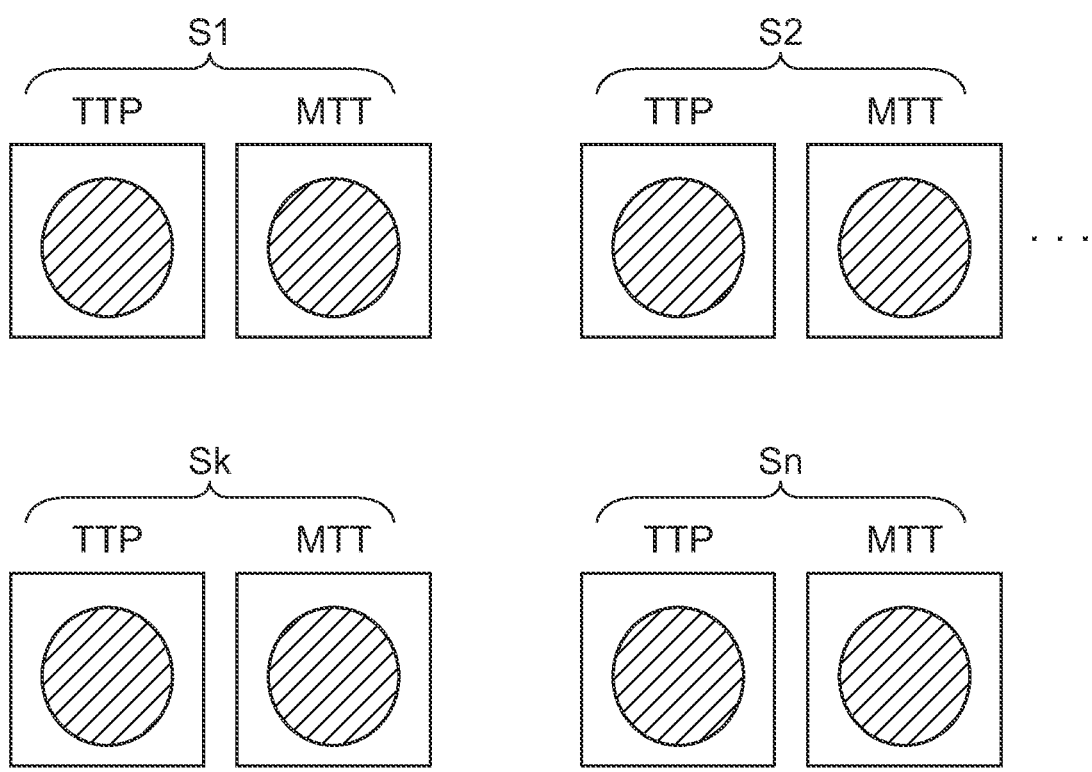

FIGS. 6A and 6B are drawings explaining two maps generated with respect to each of the slices S1 to Sn.

FIG. 6A is a drawing schematically illustrating two maps generated with respect to each of the slices S1 to Sn.

The map generation device 63 generates two maps (TTP map and MTT map) with respect to each of the slices S1 to Sn. The maps respectively represent the following parameters:
TTP map: peak concentration arrival time TTP
MTT map: mean transit time MTT FIG. 6B is a drawing schematically illustrating the two maps with respect to the slice Sk.

In FIG. 6B, the differences in the magnitude of pixel value between the pixels in the TTP map are represented by the shade of gray of each pixel. The color of a pixel comes closer to white with increase in peak concentration arrival time TTP and the color of a pixel comes closer to black with reduction in peak concentration arrival time TTP.

The above description refers to the TTP map. However, the MTT map can also be described similarly with the TTP map.

After the generation of the TTP maps and the MTT maps, the flow proceeds to Step S4.

At Step S4, a window width WW and a window level WL used to display each TTP map and MTT map are computed. In this embodiment, the expression for computing the window width WW is indicated by Expression (7) described later and the expression for computing the window level WL is indicated by Expression (8) described later. When a lesion exists in the brain of the subject, the following can be implemented by computing the window width WW and the window level WL according to Expressions (7) and (8): the TTP map and the MTT map can be displayed so that a lesion region in the brain and an unaffected region where no lesion exists can be visually and easily discriminated from each other. As mentioned above, an unaffected region and a lesion region in a brain can be visually and easily discriminated from each other by computing the window width WW and the window level WL according to Expressions (7) and (8) described later. Hereafter, the reason for this will be described with reference to FIG. 7 to FIG. 9.

Figure 7:
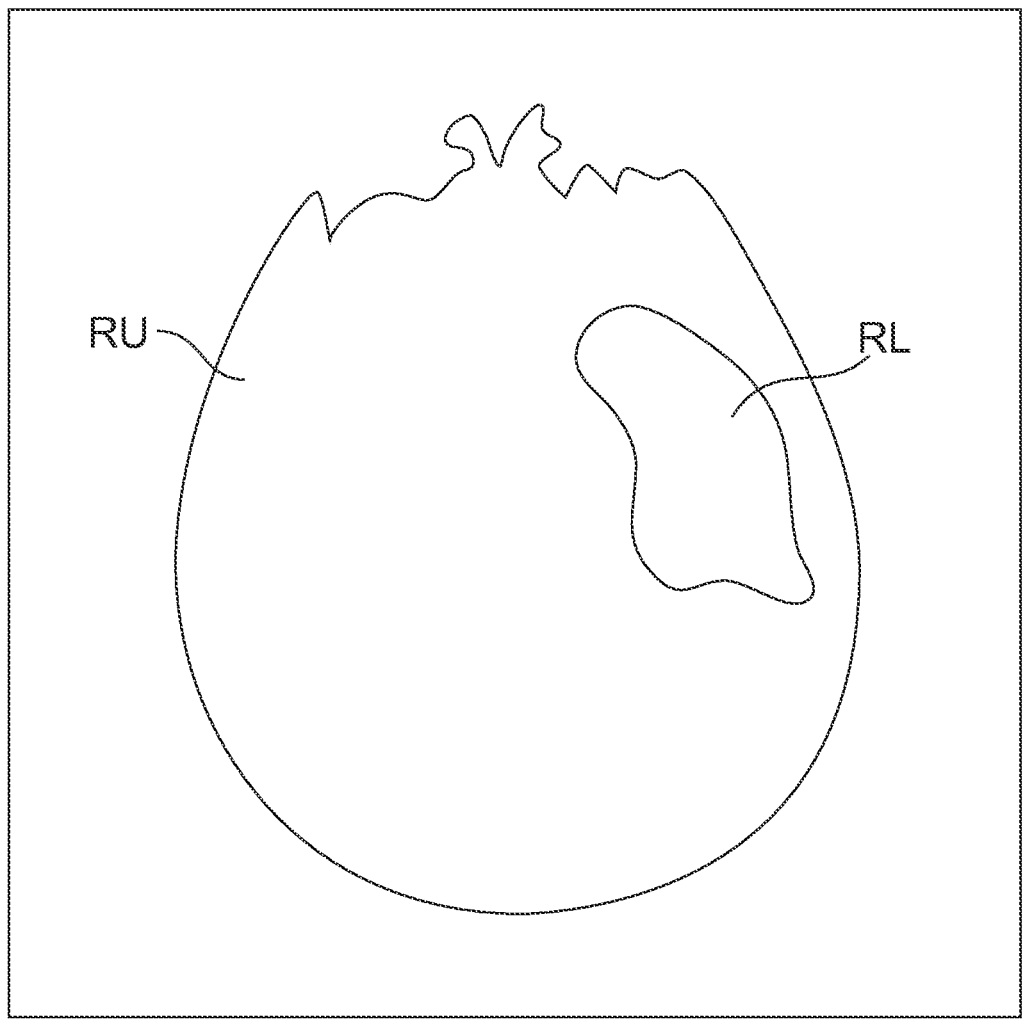
FIG. 7 is a drawing schematically illustrating an example of a TTP map obtained when a lesion has occurred in a brain.
Figure 8A:
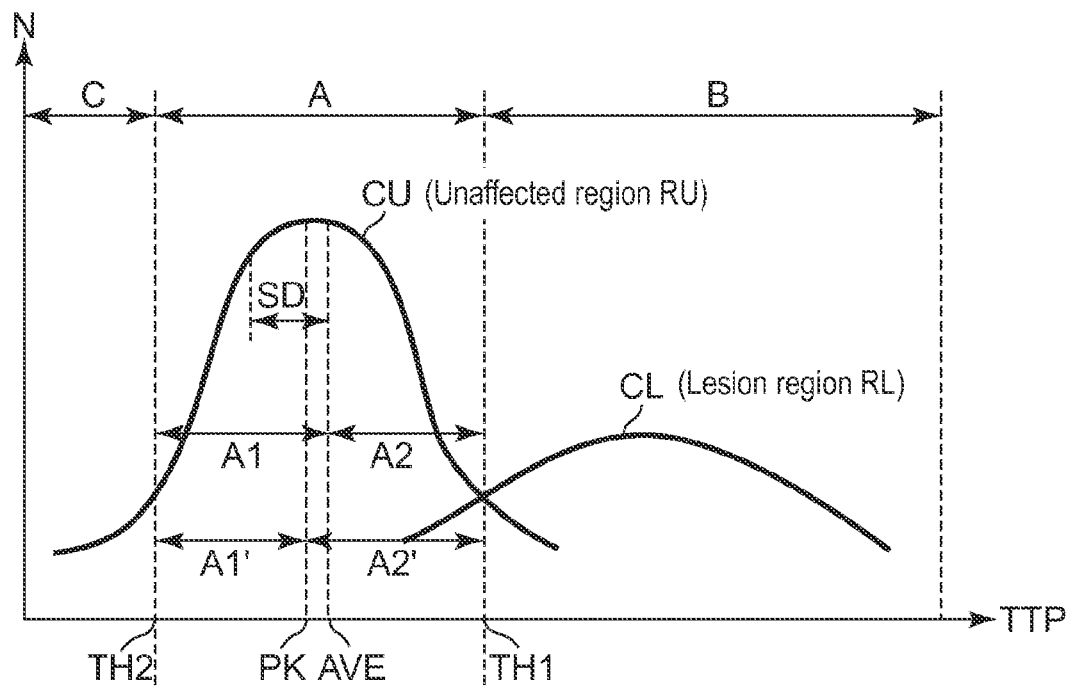
FIGS. 8A and 8B are drawings illustrating an example of window width WW and window level WL set for the TTP map illustrated in FIG. 7.
Figure 8B:
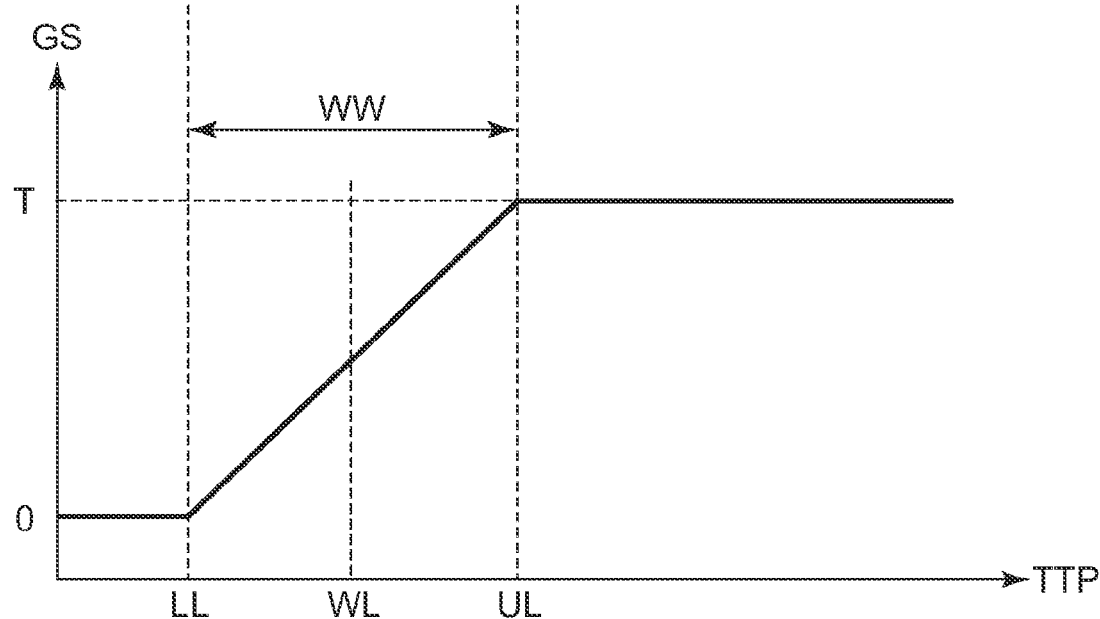

FIG. 7 illustrates an example of a diagrammatic sketch of a TTP map obtained when a lesion is contained in a section of a slice; and FIGS. 8A and 8B are drawings illustrating an example of a window width WW and a window level WL set for the TTP map illustrated in FIG. 7.

FIG. 7 illustrates an example where a lesion region RL has occurred on the right side of a brain. The area around the lesion region RL is an unaffected region RU where no lesion has occurred.

FIG. 8A is a graph explaining a difference in peak concentration arrival time TTP between the unaffected region RU and lesion region RL illustrated in FIG. 7.

In the graph in FIG. 8A, two distribution curves CU and CL indicating the distribution of the values of peak concentration arrival time TTP are shown. The horizontal axis of the graph indicates peak concentration arrival time TTP and the vertical axis indicates the number N of pixels identical in the value of peak concentration arrival time TTP. The curve CU schematically indicates the distribution of the values of peak concentration arrival time TTP in the unaffected region RU. The curve CL schematically indicates the distribution of the values of peak concentration arrival time TTP in the lesion region RL.

As is apparent from the two curves CU and CL, the following is known: in the unaffected region RU, the peak concentration arrival time TTP of each pixel is prone to take a small value; and in the lesion region RL, meanwhile, the peak concentration arrival time TTP of each pixel is prone to take a relatively large value.

With reference to FIG. 8A, the peak concentration arrival time TTP can be divided into three ranges A, B, and C. The range A is a range within which the peak concentration arrival time in the unaffected region RU is concentrated and the range B is a range within which the peak concentration arrival time in the lesion region RL is concentrated. The range C is a range within which the value of peak concentration arrival time TTP is too small and there is a high possibility of noise.

On the axis of peak concentration arrival time TTP, two threshold values TH1 and TH2 are indicated. The threshold value TH1 is a value of peak concentration arrival time TTP for discriminating the following ranges from each other: the range A within which the peak concentration arrival time in the unaffected region RU is concentrated and the range B within which the peak concentration arrival time in the lesion region RL is concentrated. The threshold value TH2 is a value of peak concentration arrival time TTP for discriminating the following ranges from each other: the range A within which the peak concentration arrival time in the unaffected region RU is concentrated and the range C within which there is a high possibility of noise.

FIG. 8B is a drawing illustrating an example of the setting of window width WW and window level WL. FIG. 8B illustrates an example of the window width WW and the window level WL used in the following case: a case where the TTP map is displayed by gradient values 0 to T (for example, T=255 in case of display with a 256-step gradation) according to the value of peak concentration arrival time TTP.

The window width WW and the window level WL are represented by Expressions (1) and (2) below:

$$WW = UL - LL \qquad (1)$$

$$WL = (UL + LL)/2 \qquad (2)$$

where, UL is the upper limit value of window width WW and LL is the lower limit value of window width WW.

In FIGS. 8A and 8B, the upper limit value UL of the window width WW agrees with the threshold value TH1 of peak concentration arrival time TTP; and the lower limit value LL of window width WW agrees with the threshold value TH2 of peak concentration arrival time TTP. Therefore, Expressions (1) and (2) are represented as below:

$$WW=TH1-TH2 \quad (3)$$

$$WL=(TH1+TH2)/2 \quad (4)$$

Figure 9:
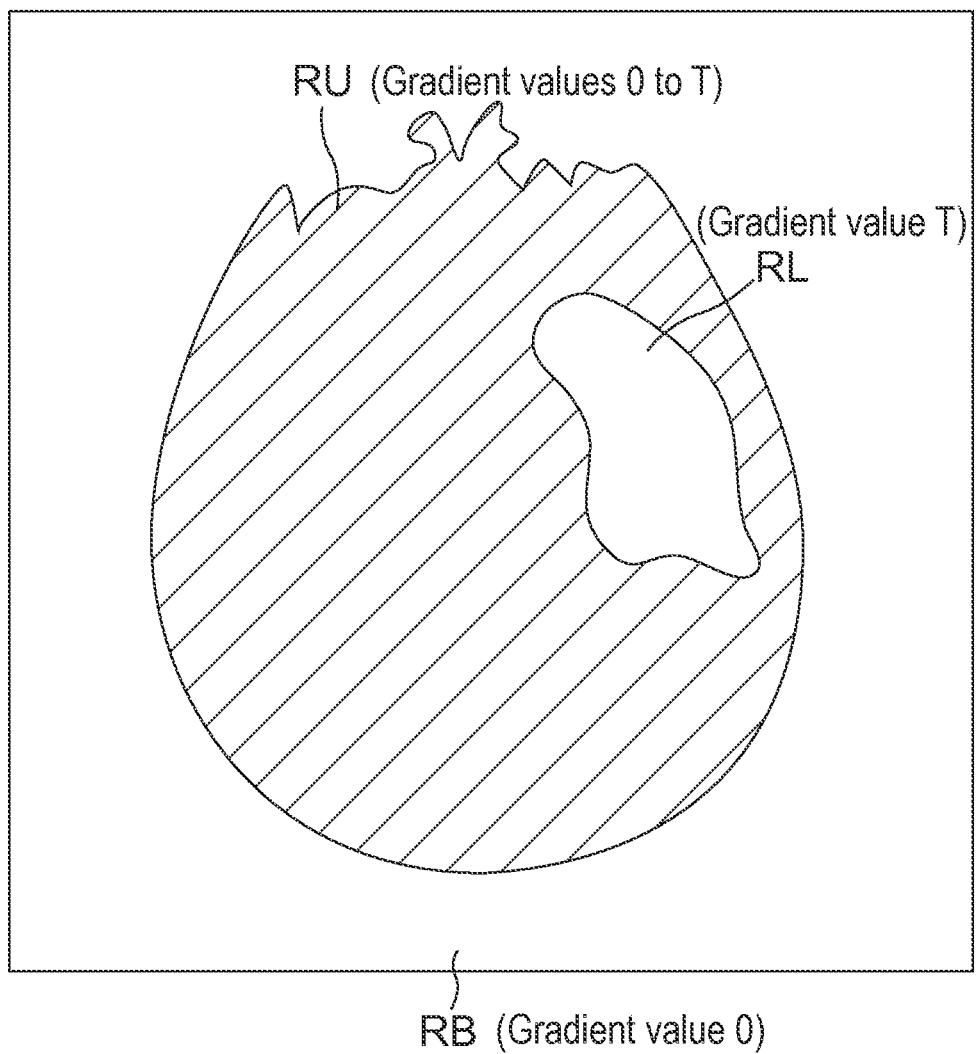
FIG. 9 is a drawing schematically illustrating a TTP map displayed using the window width WW and window level WL indicated in FIG. 8(b).

Using the window width WW and window level WL expressed by Expressions (3) and (4), the TTP map is shown in FIG. 9.

FIG. 9 is a drawing illustrating how the diagrammatic sketch of TTP map in FIG. 7 is displayed using the window width WW and window level WL indicated in FIG. 8B.

In FIG. 9, the region displayed by all the gradient values 0 to T is indicated by hatching and the regions displayed by the gradient value 0 or the gradient value T are indicated as unhatched areas. When the window width WW and the window level WL are represented by Expressions (3) and (4), the following takes place: the range of window width WW agrees with the range A within which the peak concentration arrival time in the unaffected region RU is concentrated as indicated in FIGS. 8A and 8B. Therefore, most of the unaffected region RU is displayed using the gradient values 0 to T.

Meanwhile, since the range B within which the peak concentration arrival time in the lesion region RL is concentrated deviates from the window width WW (Refer to FIGS. 8A and 8B), it is displayed by one gradient value T. The background region RB is represented by one gradient value 0.

In FIG. 9, while the unaffected region RU is displayed using the gradient values 0 to T, the lesion region RL is displayed by one gradient value T. Therefore, it is possible to visually and easily discriminate between the unaffected region RU and the lesion region RL.

Therefore, the following can be implemented by computing the threshold values TH1 and TH2 of peak concentration arrival time TTP and substituting the computed threshold values TH1 and TH2 into Expressions (3) and (4): the TTP map can be displayed so that the unaffected region RU and the lesion region RL, can be visually and easily discriminated from each other. Hereafter, description will be given to computation methods for the threshold values TH1 and TH2 with reference to FIGS. 8A and 8B.

In FIG. 8A, the mean value AVE of the peak concentration arrival time TTP of the pixels in the unaffected region RU is indicated. The following relation shows in Expression (5) between the mean value AVE and the threshold value TH1:

$$TH1=AVE+A2 \quad (5)$$

where, A2 is the time difference between the threshold value TH1 and the mean value AVE.

The threshold value TH1 and the mean value AVE largely vary from subject to subject. Meanwhile, it has been found from clinical data that the time difference A2 does not vary so much from subject to subject. In this embodiment, consequently, an appropriate value is determined as the time difference A2 from clinical data beforehand and the determined value of time difference A2 is stored beforehand in the storage unit 646 (Refer to FIG. 1). In this embodiment, therefore, the value stored in the storage unit 646 beforehand is used for the time difference A2 on the right-hand side of Expression (5). To compute the threshold value TH1 as indicated by Expression (5), it is required to know the mean value AVE in addition to the time difference A2. However, the mean value AVE can be computed by the method described later. Since two terms, AVE and A2, on the right-hand side of Expression (5) are determined, therefore, the threshold value TH1 can be computed.

The threshold value TH2 is also determined using the mean value AVE similarly with the threshold value TH1. The threshold value TH2 is expressed by Expression (6) using the mean value AVE:

$$TH2=AVE-A1 \quad (6)$$

where, A1 is the time difference between the threshold value TH2 and the mean value AVE.

The mean value AVE can be computed by the method described later and A1 can also be computed by the method described later; therefore, the threshold value TH2 can be computed.

Substituting Expressions (5) and (6) into Expression (3), the window width WW can be expressed by Expression (7) below:

$$WW=TH1-TH2=(AVE+A2)-(AVE-A1)=A2+A1 \quad (7)$$

Substituting Expressions (5) and (6) into Expression (4), the window level WL can be expressed by Expression (8) below:

$$WL=(TH1+TH2)/2=\{(AVE+A2)+(AVE-A1)\}/2=AVE+(A2-A1)/2 \quad (8)$$

The following is apparent from Expressions (7) and (8): the window width WW and the window level WL of the TTP map can be determined by the mean value AVE, time difference A1, and time difference A2.

The description with reference to FIG. 7 to FIG. 9 refers to methods for determining the window width WW and window level WL of a TTP map. Methods for determining the window width WW and window level WL of an MTT map can also be similarly described.

In this embodiment, Step S4 (Refer to FIG. 2) includes Steps S41 to S49 so that the window width WW and the window level WL can be computed using Expressions (7) and (8). Hereafter, description will be given to each of Steps S41 to S49.

At Step S41, the display device 8 displays the TTP map and MTT map (Refer to FIG. 6) of the slice Sk generated at Step S3 in response to an instruction from the display control device 641 (Refer to FIG. 1).

Figure 10:
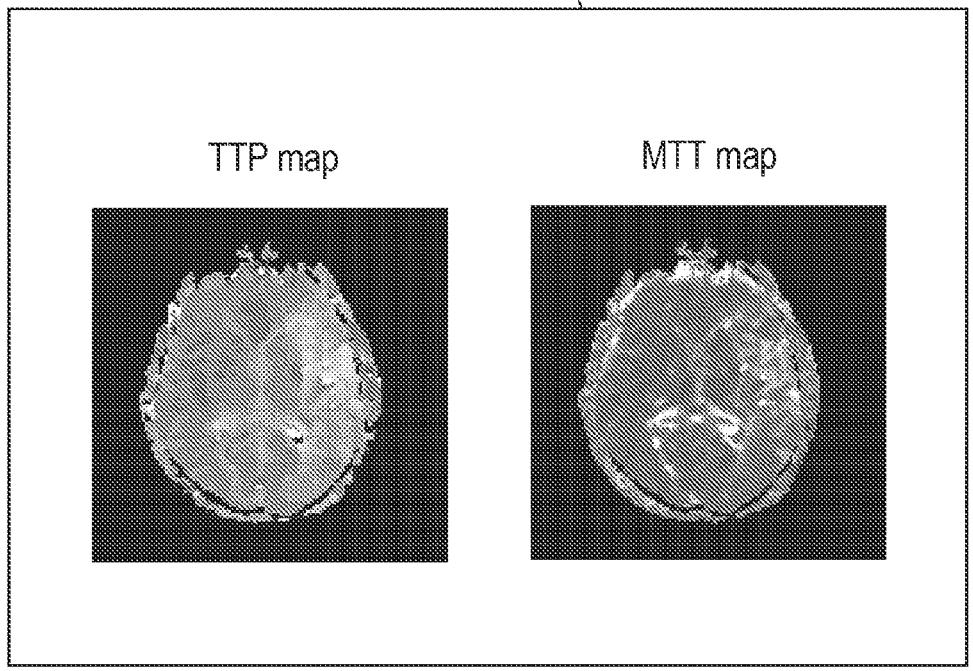
FIG. 10 is a drawing illustrating the TTP map and MTT map of slice Sk displayed on a display device 8.

FIG. 10 illustrates the TTP map and MTT map of the slice Sk displayed on the display device 8.

On the screen 8a of the display device 8, the TTP map and MTT map of the slice Sk are displayed. After the maps are displayed, the flow proceeds to Step S42.

At Step S42, the operator 10 performs the following operation with reference to the displayed TTP map and MTT map of the slice Sk: the operator searches for an unaffected region where no lesion has occurred in the sections of the slice Sk and sets a region of interest in the unaffected region.

Figure 11:
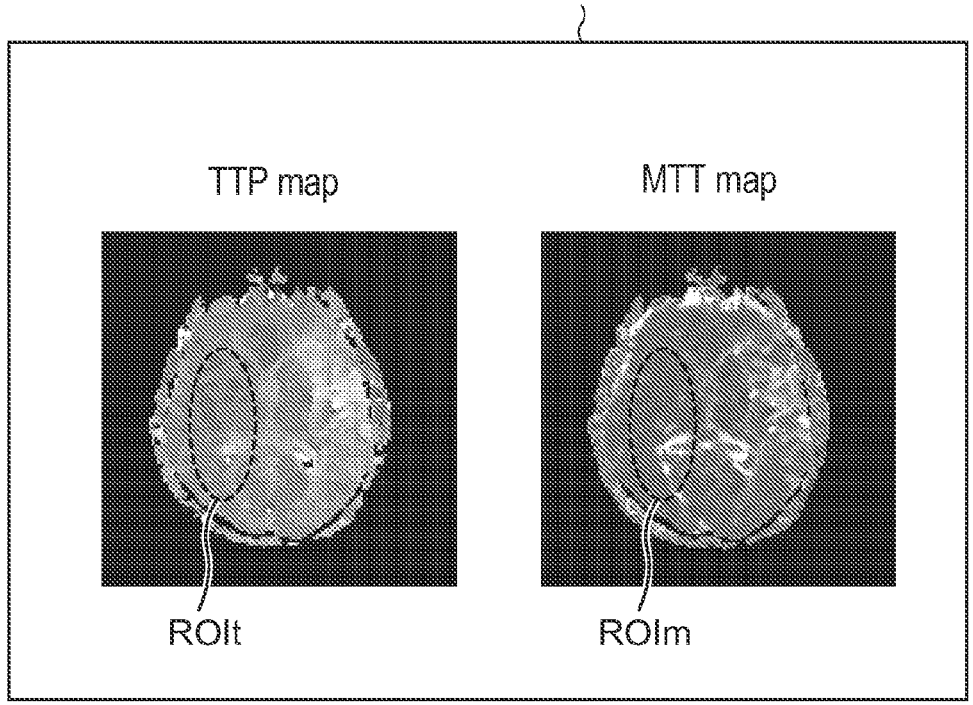
FIG. 11 is a drawing illustrating how a region of interest is set in an unaffected region.

FIG. 11 illustrates how a region of interest is set in an unaffected region.

The operator 10 operates the input device 7 to set a region of interest ROIt over the TTP map displayed on the screen 8a of the display device. As the result of the operator 10 setting the region of interest ROIt over the TTP map, a region of interest ROIm corresponding to the region of interest ROIt in the TTP map is automatically displayed over the MTT map. After the setting of the regions of interest ROIt and ROIm, the flow proceeds to Step S43.

At Step S43, the distribution computation device 642 (Refer to FIG. 1) computes the distribution of the values of peak concentration arrival time TTP of the pixels contained in the region of interest ROIt in the TTP map. Description will be continued on the assumption that in this embodiment, the computed distribution is represented by the curve CU shown in FIG. 8A. After the computation of the distribution of the values of peak concentration arrival time TTP represented by the curve CU, the flow proceeds to Step S44.

At Step S44, the mean value computation device 643 (Refer to FIG. 1) computes the mean value AVE (Refer to FIG. 8A) of the peak concentration arrival time TTP of each pixel in the curve CU. After the computation of the mean value AVE of peak concentration arrival time TTP, the flow proceeds to Step S45.

At Step S45, the standard deviation computation device 644 (Refer to FIG. 1) computes the standard deviation SD (Refer to FIG. 8A) of peak concentration arrival time TTP in the curve CU. The standard deviation SD is a value used to compute the time difference A1. After the computation of the standard deviation SD, the flow proceeds to Step S46.

At Step S46, the time difference setting device 645 (Refer to FIG. 1) sets the value of time difference A2 contained on the right-hand sides of Expressions (7) and (8). To set the value of time difference A2, the time difference setting device 645 accesses the storage unit 646 and reads the time difference A2 stored beforehand.

Figure 12:
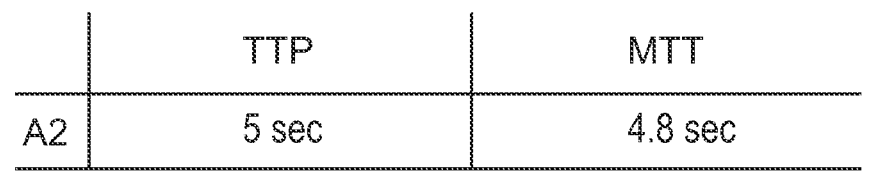

FIG. 12 is a schematic diagram indicating values stored in the storage unit 646.

In the storage unit 646, there are stored the time difference A2 related to peak concentration arrival time TTP and the time difference A2 related to mean transit time MTT. In this embodiment, the time difference A2 related to peak concentration arrival time TTP is 5 seconds and the time difference A2 related to mean transit time MTT is 4.8 seconds. These values (5 seconds and 4.8 seconds) are values determined based on clinical data. When the peak concentration arrival time TTP and the mean transit time MTT are compared with each other, it is apparent from FIG. 12 that they are different in the value of time difference A2.

The time difference setting device 645 sets the time difference A2 related to the TTP map. Therefore, from among 5 seconds and 4.8 second stored in the storage unit 646, it sets 5 seconds as the time difference A2 related to the TTP map. After the setting of the time difference A2 related to the TTP map, the flow proceeds to Step S47.

At Step S47, the time difference computation device 647 (Refer to FIG. 1) sets the value of time difference A1 contained on the right-hand sides of Expressions (7) and (8). In this embodiment, the time difference A1 is computed by Expression (9) below:

$$A1 = scale * SD \quad (9)$$

where, scale is a scale value and SD is standard deviation.

As indicated by Expression (9), the time difference A1 is a value obtained by multiplying standard deviation SD by a scale value scale. In this embodiment, the scale value scale is scale=2. However, it need not always be scale=2 and any other value may be adopted as required.

The standard deviation SD in Expression (9) has been computed at Step S45. Therefore, the time difference A1 is computed by substituting the computed standard deviation SD into Expression (9). After the computation of the time difference A1, the flow proceeds to Step S48.

At Step S48, the display condition computation device substitutes the mean value AVE computed at Step S44, the time difference A2 set at Step S46, and the time difference A1 computed at Step S47 into Expressions (7) and (8). As a result, the window width WW and window level WL with respect to the TTP map are computed. The computed window width WW and window level WL are set as indicated in FIG. 8B. Therefore, most of the unaffected region RU is displayed using the gradient values 0 to T but most of the lesion region RL is displayed by only the gradient value T.

The window width WW and window level WL with respect to the TTP map computed at Step S48 are used in common for the TTP maps of all the slices S1 to Sn.

After the computation of the window width WW and window level WL with respect to the TTP map, the flow proceeds to Step S49.

At Step S49, it is determined whether or not the window width WW and the window level WL have been computed with respect to all the maps. In the above description, the window width WW and window level WL with respect to the TTP map were computed but the window width WW or window level WL with respect to the MTT map has not been computed yet. Consequently, the flow returns to Step S43.

At Step S43, the distribution computation device 642 (Refer to FIG. 1) computes the distribution of the values of mean transit time MTT of the pixels contained in the region of interest ROIm (Refer to FIG. 11) in the MTT map. After the computation of this distribution, the window width WW and window level WL with respect to the MTT map are computed by carrying out the processing of Step S44 to Step S48 as mentioned above. To compute the window width WW and window level WL with respect to the MTT map, the following processing is carried out at Step S46: among 5 seconds and 4.8 seconds stored in the storage unit 646 (Refer to FIG. 12), 4.8 seconds is set as the time difference A2 with respect to the MTT map.

After the computation of the window width WW and window level WL with respect to the MTT map, the flow proceeds to Step S49.

At Step S49, it is determined whether or not the window width WW and the window level WL have been computed with respect to all the maps. Since the window width WW and the window level WL have been computed with respect to all of both the maps, TTP maps and MTT maps, the flow proceeds to Step S5.

At Step S5, the display device 8 displays a TTP map and an MTT map in accordance with the window width WW and window level WL computed at Step S48.

FIG. 13 illustrates a TTP map and an MTT map displayed on the display device 8 in accordance with the window width WW and window level WL computed at Step S48.

It is apparent from FIG. 13 that regions displayed by the same gradient value appear in the TTP map and the MTT map. The areas displayed in white in FIG. 13 are a lesion region RL where a lesion is suspected to exist. Therefore, the following is understood from the comparison of FIG. 11 and FIG. 13: the unaffected region RU and the lesion region RL can be visually and easily discriminated from each other by displaying the TTP map and the MTT map as illustrated in FIG. 13.

In this embodiment, the following processing is carried out to compute the distribution of the values of peak concentration arrival time TTP in an unaffected region at Step S42: the operator 10 manually sets a region of interest ROI in the unaffected region. Instead, the distribution of the values of peak concentration arrival time TTP in an unaffected region may be computed by automatically detecting the unaffected region.

In this embodiment, Expressions (7) and (8) are used to compute WL and WW. Instead, any other expression different from Expressions (7) and (8) may be used to compute WL and WW.

In this embodiment, WW and WL with respect to the TTP map and the MTT map are computed. Instead, any other map (BV map, CBF map, BAT map, TTP map, or the like) may be used.

In this embodiment, the mean value AVE, time difference A1, and time difference A2 are used to define the window width WW and the window level WL (Refer to Expressions (7) and (8)). Instead, any other value different from AVE, A1, and A2 may be used to define the window width WW and the window level WL. For example, the following three values indicated in FIGS. 8A and 8B may be used to define the window width WW and the window level WL: (1) Peak value PK of peak concentration arrival time TTP in the curve CU; (2) Time difference A1' between peak value PK and threshold value TH1; and (3) Time difference A2' between peak value PK and threshold value TH2.

When peak value PK, time difference A1', and time difference A2' are used, the window width WW and the window level WL are defined by Expressions (10) and (11) below:

$$WW = A2' + A1' \quad (10)$$

$$WL = PK + (A2' - A1')/2 \quad (11)$$

When Expressions (10) and (11) are used to compute the window width WW and window level WL, the time difference A2' can be stored beforehand in the storage unit 646 (Refer to FIG. 1). In place of the peak value PK of peak concentration arrival time TTP in the curve CU, a median may be used to define the expressions of the window width WW and the window level WL.

Many widely different embodiments of the invention may be configured without departing from the spirit and the scope of the present invention. It should be understood that the present invention is not limited to the specific embodiments described in the specification, except as defined in the appended claims.

What is claimed is:

1. A blood flow dynamic analysis apparatus for use in analyzing kinetics of blood flow in a subject after a contrast medium has been injected into the subject, the blood flow dynamic analysis apparatus comprising:
a map generation device configured to compute a value of a parameter related to time change in a concentration of the contrast medium injected into the subject and to generate a map of the parameter; and
a display condition determination device comprising:
a reference value computation unit configured to compute a reference value of the parameter in the unaffected region in the map; and
a standard deviation computation unit configured to compute a standard deviation of the parameter in the unaffected region in the map, wherein the display condition determination device is configured to determine a display condition for the map based on a threshold value of the parameter for discriminating between a lesion region where a lesion exists and an unaffected region where no lesion exists in the map, to determine the display condition for the map based on a difference between the reference value of the parameter in the unaffected region in the map and the threshold value of the parameter, to store beforehand the difference between the reference value of the parameter in the unaffected region in the map and the threshold value of the parameter, and to compute the display condition for the map based on the reference value of the parameter, the difference between the reference value of the parameter and the threshold value of the parameter stored beforehand, and the standard deviation of the parameter.

2. The blood flow dynamic analysis apparatus according to claim 1, wherein the reference value of the parameter is one of a mean value of the parameter in the unaffected region in the map, a peak value of the parameter in the unaffected region in the map, and a median value of the parameter in the unaffected region in the map.

3. The blood flow dynamic analysis apparatus according to claim 1, wherein the parameter is at least one of a time to peak (TTP) value and a mean transit time (MTT) value.

4. The blood flow dynamic analysis apparatus according to claim 1, wherein the map generation device is configured to compute values of a plurality of parameters related to time change in the concentration of the contrast medium and to generate a plurality of maps, wherein each of the plurality of maps is associated with one parameter, and wherein the display condition determination device is configured to determine a display condition for the plurality of maps.

5. The blood flow dynamic analysis apparatus according to claim 4, wherein the plurality of parameters include at least a time to peak (TTP) value and a mean transit time (MTT) value.

6. The blood flow dynamic analysis apparatus according to claim 1, wherein the display condition is at least one of a window width and a window level.

7. A magnetic resonance imaging system comprising:
a contrast medium injection device configured to inject a contrast medium into a subject; and
a blood flow dynamic analysis apparatus comprising:
a map generation device configured to compute a value of a parameter related to time change in a concentration of the contrast medium injected into the subject and to generate a map of the parameter; and
a display condition determination device comprising:
a reference value computation unit configured to compute a reference value of the parameter in the unaffected region in the map; and
a standard deviation computation unit configured to compute a standard deviation of the parameter in the unaffected region in the map, wherein the display condition determination device is configured to determine a display condition for the map based on a threshold value of the parameter for discriminating between a lesion region where a lesion exists and an unaffected region where no lesion exists in the map, to determine the display condition for the map based on a difference between the reference value of the parameter in the unaffected region in the map and the threshold value of the parameter, to store beforehand the difference between the reference value of the parameter in the unaffected region in the map and the threshold value of the parameter, and to compute the display condition for the map based on the reference value of the parameter, the difference between the reference value of the parameter and the threshold value of the parameter stored beforehand, and the standard deviation of the parameter.

8. A blood flow dynamic analysis method for analyzing the kinetics of a blood flow in a subject, the blood flow dynamic analysis method comprising:
injecting a contrast medium into a subject;
computing a value of a parameter related to time change in a concentration of the contrast medium;
generating a map of the parameter;
determining a display condition for the map based on a threshold value of the parameter for discriminating between a lesion region where a lesion exists and an unaffected region where no lesion exists in the map;

determining the display condition for the map based on a difference between a reference value of the parameter in the unaffected region in the map and the threshold value of the parameter;

storing beforehand the difference between the reference value of the parameter in the unaffected region in the map and the threshold value of the parameter; and computing the display condition for the map based on the reference value of the parameter, the difference between the reference value of the parameter and the threshold value of the parameter stored beforehand, and a standard deviation of the parameter in the unaffected region of the map.

* * * * *